United States Patent [19]

Rizzo

[11] 4,413,013

[45] Nov. 1, 1983

[54] SULFONAMIDE COMPOUNDS, COMPOSITIONS AND METHODS FOR COMBATTING INSECTS

[75] Inventor: Victor L. Rizzo, Almena Township, Van Buren County, Mich.

[73] Assignee: The Upjohn Company, Kalamazoo, Mich.

[21] Appl. No.: 330,740

[22] Filed: Dec. 14, 1981

Related U.S. Application Data

[63] Continuation of Ser. No. 51,258, Jun. 22, 1979, abandoned, which is a continuation of Ser. No. 898,570, Apr. 21, 1978, abandoned.

[51] Int. Cl.³ .................. A01N 9/16; C07C 143/75; C07C 143/79
[52] U.S. Cl. .................. 424/321; 260/465 E; 424/304; 564/87; 564/89; 564/91; 564/99
[58] Field of Search .................. 564/87, 89, 91, 99; 260/465 E; 424/304, 321

[56] References Cited

U.S. PATENT DOCUMENTS

| | | | |
|---|---|---|---|
| 3,285,929 | 11/1966 | Klauke et al. | 424/321 X |
| 3,939,192 | 2/1976 | Kühle et al. | 424/298 X |
| 3,947,591 | 3/1976 | Rizzo et al. | 564/100 X |
| 3,998,969 | 12/1976 | Rizzo | 424/324 |
| 4,115,583 | 9/1978 | Böger et al. | 564/101 X |
| 4,246,283 | 1/1981 | Böger et al. | 564/91 X |
| 4,356,191 | 10/1982 | DeGeeter | 424/321 |

FOREIGN PATENT DOCUMENTS 867985 12/1978 Belgium .

*Primary Examiner*—Thomas A. Waltz
*Attorney, Agent, or Firm*—John J. Killinger; Sidney B. Williams, Jr.

[57] ABSTRACT

Novel pesticidal N-[[[arylformimidoyl]methylamino]-thio]-N-substituted sulfonamides are disclosed with novel compositions thereof and methods for their use in controlling invertebrate arthropod pests, particularly insects, mites, and ticks.

39 Claims, No Drawings

SULFONAMIDE COMPOUNDS, COMPOSITIONS AND METHODS FOR COMBATTING INSECTS

CROSS REFERENCE TO RELATED APPLICATIONS

This application is a continuation of application Ser. No. 051,258, filed June 22, 1979, now abandoned, which is a continuation of application Ser. No. 898,570, filed Apr. 21, 1978, now abandoned.

BACKGROUND OF THE INVENTION

1. Field of the Invention

The invention concerns novel N-[[[arylformimidoyl]-methylamino]thio]-N-substituted sulfonamides, pesticidal compositions thereof, and their use for killing and otherwise controlling arthropod pests.

2. Description of the Prior Art

A number of N-alkyl-N'-aryl formamidines have been previously described as pesticides; see, for example, Belgian Pat. Nos. 760,141; 770,825 and German Pat. Nos. 1,172,081; 2,202,034.

N-sulfenylated chlorides of sulfonamides are known; for example, German Pat. Nos. 1,101,407 and 1,156,403.

Arylsulfenylated formamidines and aminosulfenylated formamidines are known and used as insecticides; for example, U.S. Pat. Nos. 3,887,619 and 3,947,591 and 3,998,969.

SUMMARY OF THE INVENTION

The invention comprises compounds selected from those of the formula:

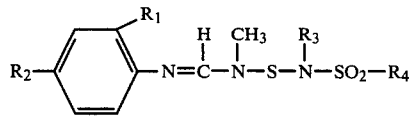

(1)

wherein $R_1$ is chloro, bromo, or alkyl of one through four carbon atoms; $R_2$ is hydrogen, chloro, bromo, or alkyl of one through four carbon atoms; $R_3$ is (1) alkyl of one through eight carbon atoms, (2) cycloalkyl of five through eight carbon atoms, (3) phenalkyl wherein alkyl is one or two methylene units in length, or (4) phenyl where the phenyl is unsubstituted or substituted with one through three substituents selected from the group consisting of methyl, chloro, bromo, nitro, trifluoromethyl, alkoxy of one or two carbon atoms, and cyano; and $R_4$ is (1) alkyl of one through four carbon atoms, (2) phenalkyl wherein alkyl is one or two methylene units in length and where the phenyl is unsubstituted or substituted with one through three substituents selected from the group consisting of methyl, chloro, bromo, nitro, trifluoromethyl, alkoxy of one or two carbon atoms, and cyano, or (3) phenyl where the phenyl is unsubstituted or substituted with a substituent selected from the group consisting of methyl, chloro and bromo.

The invention also comprises compounds of formula I wherein $R_1$ is chloro or bromo; $R_2$ is alkyl of 1 through 4 carbon atoms, chloro, or bromo; and $R_3$ and $R_4$ are as defined above.

The invention also comprises compounds of formula I wherein $R_1$ and $R_2$ are chloro or bromo and $R_3$ and $R_4$ are as defined above.

The invention also comprises compositions for arthropod control which comprise an acceptable carrier and an effective amount of a compound of the invention.

The sulfonamidosulfenyl formamidine derivatives of this invention are particularly advantageous commercially as invertebrate pesticides because they are more stable than, for example, the aminosulfenylated formamidines both in storage and upon application in the field, thus providing a long-lasting residual effectiveness.

In addition to killing invertebrate pests on contact, the compounds of the invention are absorbed by the vascular system of many plants, for example by cotton plants, and act systemically to kill the pests feeding upon the plant. Thus their period of pesticidal activity is further extended and non-feeding arachnids and insects, e.g. insects not harmful to the plant, are not unnecessarily killed during the whole period of pesticidal activity.

Compounds of the invention are also ovicidal, and are particularly effective in the control of acarine pest populations by this ovicidal action. Lepidopterous ova are also particularly susceptible to the compounds of the invention.

The compounds of the invention are also advantageous in that they exhibit relatively low mammalian toxicity and are non-phytotoxic at effective concentrations.

Compounds of the invention having the formula:

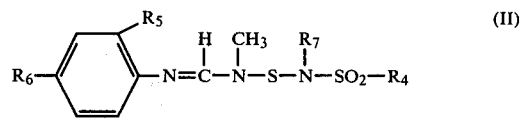

(II)

wherein $R_5$ is methyl or chloro; $R_6$ is methyl or chloro; $R_7$ is (1) alkyl of one through four carbon atoms, (2) cycloalkyl of five through eight carbon atoms, (3) phenalkyl wherein alkyl is one or two methylene units in length, or (4) phenyl where the phenyl is unsubstituted or substituted with one through three substituents selected from the group consisting of methyl, chloro, and bromo; and $R_4$ is (1) alkyl of one through four carbon atoms, (2) phenalkyl wherein alkyl is one or two methylene units in length and where the phenyl is unsubstituted or substituted with one through three substituents selected from the group consisting of methyl, chloro, bromo, nitro, trifluoromethyl, alkoxy of one or two carbon atoms, and cyano, or (3) phenyl where the phenyl is unsubstituted or substituted with a substituent selected from the group consisting of methyl, chloro, and bromo are preferred for their greater pesticidal effect and chemical stability.

DETAILED DESCRIPTION OF THE INVENTION

The compounds of this invention (I) can be synthesized by the reaction of an N-alkyl-N'-arylformamidine (III) with an N-substituted sulfonamide-N-sulfenyl chloride (IV) in an inert solvent, such as benzene, tetrahydrofuran, methylene chloride, or carbon tetrachloride, in the presence of an acid acceptor such as a tertiary amine. The reaction which occurs is illustrated by the schematic formula:

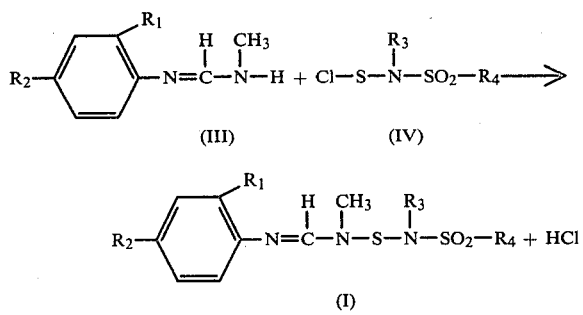

wherein $R_1$, $R_2$, $R_3$, and $R_4$ are as described above.

The above illustrated reaction is advantageously carried out in the presence of an inert organic solvent. An inert organic solvent is defined herein as a solvent for the formamidine reactant (III) which does not enter into reaction with the reaction mixture components or in any way alter the desired course of the reaction. Illustrative of inert organic solvents are tetrahydrofuran, benzene, diethylether, and methylene chloride. Preferred as the inert organic solvent is methylene chloride.

The proportion of solvent employed is not critical, but advantageously is a sufficient quantity to solubilize the reactant formamidine (III).

During the course of the above illustrated reaction, hydrochloric acid is generated as a by-product. Preferably this acid is removed from the reaction mixture as it forms. This may be accomplished by conventional and known methods, for example by adding an acid acceptor compound to the reaction mixture. Examples of acid acceptor compounds are the tertiary amines such as trimethylamine, triethylamine, tripropylamine, tributylamine, pyridine and the like.

Although the above reaction may be carried out over a broad range of temperature conditions, i.e., from about $-30°$ C. to about reflux temperature for the reaction mixture, it is preferably carried out at about $0°$ to $20°$ C.

Progress of the above reaction may be followed by conventional analytical methods, such as for example by nuclear magnetic resonance analysis which will show spectral characteristics of the product compounds I or by thin-layer chromatography which will show the appearance of product compounds. Upon completion, the desired compounds I are readily separated from the reaction mixture by conventional methods such as by filtration to remove solid residues, distillation to remove solvents, and recrystallization or silica gel chromatography.

Sulfonamide-N-sulfenyl chlorides (IV) are known in the literature and can be prepared by chlorination of an N,N'-dithiobissulfonamide, German Pat. No. 1,101,407 issued Sept. 28, 1961, or by reaction of an N-substituted sulfonamide with sulfur dichloride in the presence of a tertiary amine. German Pat. No. 1,156,403 issued Oct. 31, 1963. N,N'-dithiobissulfonamides can be generated by reacting an N-substituted sulfonamide with sulfur monochloride in the presence of a tertiary amine.

N-Alkyl-N'-arylformamidines (III) are also known in the literature and may be prepared by methods described in Belgium Pat. No. 770,825 issued Feb. 2, 1972, in U.S. Pat. No. 3,729,565 issued Apr. 24, 1973, and in U.S. Pat. No. 3,887,619 issued June 3, 1975.

The following examples describe the manner and process of making and using the invention and set forth the best mode contemplated by the inventor of carrying out the invention but are not to be construed as limiting.

All temperatures are in degrees centigrade.

Ambient temperature is in the range $20°$ to $25°$.

SSB refers to Skellysolve B ®, an isomeric mixture of hexanes.

NMR refers to nuclear magnetic resonance.

EXAMPLE 1

N-[[N-(4-chloro-o-tolyl)-formimidoyl]methylamino[-thio]-N-methyl-p-toluenesulfonamide To a stirred solution cooled to $-10°$ of 18.5 g. (0.1 mole) of N-methyl-p-toluenesulfonamide and 10.1 g. (0.1 mole) of triethylamine in 300 ml. of methylene chloride is added dropwise 10.3 g. (0.1 mole) sulfur dichloride. The reaction mixture is stirred at ambient temperature for 0.5 hour and cooled to $10°$. A solution of 18.3 g (0.1 mole) of N-methyl-N'-(4-chloro-o-tolyl)-formamidine and 10.1 g. (0.1 mole) triethylamine in 100 ml. of methylene chloride is added rapidly with stirring. The reaction mixture is stirred at ambient temperature for 0.5 hour and extracted successively with 300 ml. of water, 300 ml. aqueous citric acid solution containing 10.5 g. (0.05 mole) of citric acid, and 300 ml. of water. The organic layer is dried and the solvent removed under reduced pressure. The residue is chromatographed over 100 g. silica gel using Hexane:$Et_2O$:$Et_3N$ (18:2:3 by volume) to obtain 3.2 g. (8% yield) of N-[[[N-(4-chloro-o-tolyl)-formimidoyl]methylamino]thio]-N-methyl-p-toluenesulfonamide as a viscous oil.

Analysis: Calc'd for $C_{17}H_{20}ClN_3O_2S_2$: C, 51.31; H, 5.07; N, 10.56. Found: C, 51.36; H, 5.23; N, 10.72.

NMR ($CDCl_3$-tetramethylsilane) 7.95, 7.3, 3.4, 3.25, 2.35, 2.28.

EXAMPLE 2

N-[[[N-(4-chloro-o-tolyl)formimidoyl]-methylamino]-thio]-N-isopropyl-p-toluenesulfonamide To 19.5 g (0.04 mole) of N,N'-dithiobis[N-isopropyl-p-toluenesulfonamide] in 200 ml. of benzene is added dropwise 5.4 g. (0.04 mole) sulfuryl chloride in 10 ml. of benzene. The reaction mixture is heated at reflux for 1.5 hours until evolution of gas ceases, purged with nitrogen, and cooled to $10°$. A solution of 14.6 g. (0.08 mole) of N-methyl-N'-(4-chloro-o-tolyl) formamidine and 8.08 g. (0.08 mole) of triethylamine in 100 ml. of benzene is added rapidly. The mixture is stirred 15 minutes at ambient temperature and extracted consecutively with 500 ml. water, 400 ml. aqueous citric acid solution containing 8 g. citric acid, and 500 ml. water. The organic layer is dried and the solvent removed. The product is recrystallized from SSB to give 23.7 g. (68% yield) of N-[[[N-(4-chloro-o-tolyl)formimidoyl)]-methylamino]thio]-N-isopropyl-p-toluenesulfonamide as white crystals, melting point (m.p.) $99.5°-100.5°$.

Analysis: Calc'd for $C_{19}H_{24}ClN_3O_2S_2$: C, 53.57; H, 5.68; N, 9.86. Found: C, 53.97; H, 5.83; N, 9.80.

EXAMPLE 3

[[[N-2,4-xylylformimidoyl]-methylamino]thio]-N-isopropyl-p-toluenesulfonamide

To a stirred solution cooled to $-20°$ of 10.6 g. (0.05 mole) of N-isopropyl-p-toluenesulfonamide and 5.05 g. (0.05 mole) of triethylamine in 150 ml. of methylene chloride is added dropwise 3.4 g. (0.025 mole) of sulfur monochloride. The reaction mixture is stirred at ambient temperature for one hour. A solution of 1.77 g. (0.025 mole) of chlorine in 50 ml. carbon tetrachloride is added rapidly and the reaction mixture stirred for 0.5 hour. The reaction mixture is cooled to 10° and a solution of 8.1 g. (0.05 mole) of N-methyl-N'-2,4-xylylformamidine and 5.05 g. (0.05 mole) of triethylamine in 75 ml. methylene chloride is added. The mixture is stirred at ambient temperature for 0.5 hour and extracted with a solution of 10 g. citric acid in 200 ml. of water. The organic layer is dried and the solvent removed. The product is recrystallized from SSB to give 11.5 g. (57% yield) of N-[[[N-2,4-xylylformimidoyl]methylamino]-thio]-N-isopropyl-p-toluenesulfonamide as white crystals, mp. 96°-97°.

Analysis: Calc'd for $C_{20}H_{27}N_3O_2S_2$: C, 59.23; H, 6.71; N, 10.36. Found: C, 59.07; H, 6.51; N, 10.45.

EXAMPLE 4

N-[[[N-(4-chloro-o-tolyl)-formimidoyl]methylamino]-thio]-N-methylmethanesulfonamide Following the procedure of Example 1, but substituting N-methylmethanesulfonamide for N-methyl-p-toluenesulfonamide, the product is prepared and recrystallized from ether to obtain 5.3 g. (16% yield) of N-[[[N-(4-chloro-o-tolyl)-formimidoyl]methylamino]thio]-N-methylmethanesulfonamide as white crystals, mp. 83°-84°.

Analysis: Calc'd for $C_{11}H_{16}ClN_3O_2S_2$: C, 41.05; H, 5.01; N, 13.06. Found: C, 41.07; H, 5.15; N, 13.01.

EXAMPLE 5

N-[[[N-(4-chloro-o-tolyl)-formimidoyl]methylamino]-thio]-N-isopropylmethanesulfonamide Following the procedure of Example 1, but substituting N-isopropylmethanesulfonamide for N-methyl-p-toluenesulfonamide, the product is prepared. The residue is chromatographed over 800 g. silica gel using 19:1 benzene:ethyl acetate and recrystallized from isopropanol to obtain 5.5 g. (16% yield) of N-[[[N-(4-chloro-o-tolyl)-formimidoyl]methylamino]thio]-N-isopropylmethanesulfonamide as white crystals, mp. 55°-56°.

Analysis: Calc'd for $C_{13}H_{20}ClN_3O_2S_2$: C, 44.63; H, 5.76; N, 12.00. Found: C, 44.15; H, 6.01; N, 11.58.

EXAMPLE 6

N-[[[N-(4-chloro-o-tolyl)-formimidoyl]methylamino]-thio]-N-benzylmethanesulfonamide Following the procedure of Example 1, but substituting N-benzylmethanesulfonamide for N-methyl-p-toluenesulfonamide, the product is prepared. The product is recrystallized once from isopropanol followed by two recrystallizations from ether to obtain 3.2 g. (16% yield) of N-[[[N-(4-chloro-o-tolyl)formimidoyl]methylamino]thio]-N-benzylmethanesulfonamide as white crystals, mp. 94°-95°.

Analysis: Calc'd for $C_{17}H_{20}ClN_3O_2S_2$: C, 51.31; H, 5.07; N, 10.56. Found: C, 51.34; H, 5.07; N, 10.63.

EXAMPLE 7

N-[[[N-(4-chloro-o-tolyl)formimidoyl]methylamino]-thio]-N-isopropylbenzenesulfonamide Following the procedure of Example 1, but substituting N-isopropylbenzenesulfonamide for N-methyl-p-toluenesulfonamide, the product is prepared. The product is recrystallized from isopropanol to obtain 18.3 g. (44% yield) of N-[[[N-(4-chloro-o-tolyl)formimidoyl]-methylamino]thio]-N-isopropylbenzenesulfonamide as white crystals, mp. 104°-105°.

Analysis: Calc'd for $C_{18}H_{22}ClN_3O_2S_2$: C, 52.48; H, 5.38. N, 10.20. Found: C, 52.72; H, 5.51; N, 10.03.

EXAMPLE 8

N-[[[N-(4-chloro-o-tolyl)-formimidoyl]methylamino]-thio]-N-phenylmethanesulfonamide Following the procedure of Example 2, but substituting N,N'-dithiobis[N-phenylmethanesulfonamide] for N,N'-dithiobis-[N-isopropyl-p-toluenesulfonamide], the product is prepared. The product is recrystallized from isopropanol to obtain 5.0 g. (16% yield) of N-[[[N-(4-chloro-o-tolyl)-formimidoyl]methylamino]thio]-N-phenylmethanesulfonamide as white crystals, mp. 120°-121°.

Analysis: Calc'd for $C_{16}H_{18}ClN_3O_2S_2$: C, 50.06; H, 4.72; N, 10.95. Found: C, 50.01; H, 4.76; N, 10.64

EXAMPLE 9

N-[[[N-(4-chloro-o-tolyl)-formimidoyl]methylamino]-thio]-N-cyclohexylmethanesulfonamide Following the procedure of Example 2, but substituting N,N'-dithiobis[N-cyclohexylmethanesulfonamide] for N,N'-dithiobis[N-isopropyl-p-toluenesulfonamide], the product is prepared. The product is recrystallized once from isopropanol and twice from ethyl acetate to obtain 13.1 g. (20% yield) of N-[[[N-(4-chloro-o-tolyl)-formimidoyl]methylamino]thio]-N-cyclohexylmethanesulfonamide as white crystals, mp. 125°-127°.

Analysis: Calc'd for $C_{16}H_{24}ClN_3O_2S_2$: C, 49.28; H, 6.20; N, 10.78. Found: C, 49.22; H, 6.16; N, 10.77.

EXAMPLE 10

N-[[[N-(4-chloro-o-tolyl)formimidoyl]methylamine]thio]-N-isopropylbenzylsulfonamide Following the procedure of Example 2, but substituting N,N'-dithiobis[N-isopropylbenzylsulfonamide] for N,N'-dithiobis[N-isopropyl-p-toluenesulfonamide], the product is prepared. The product is recrystallized from ether to obtain 21.4 g. (51% yield) of N-[[[N-(4-chloro-o-tolyl)formimidoyl] methylamine]thio]-N-isopropylbenzylsulfonamide as white crystals, mp. 117°-118°.

Analysis: Calc'd for $C_{19}H_{24}ClN_3O_2S_2$: C, 53.57; H, 5.68; N, 9.86. Found: C, 53.75; H, 5.76; N, 9.79.

EXAMPLE 11

N-[[[N-(4-chloro-o-tolyl)formimidoyl]methylamino]-thio]-N-ethyl-p-toluenesulfonamide Following the procedure of Example 2, but substituting N,N'-dithiobis[N-ethyl-p-toluenesulfonamide] for N,N'-dithiobis[N-isopropyl-p-toluenesulfonamide], the product is prepared. The product is recrystallized from isopropanol to obtain 20.9 g. (63% yield) of N-[[[N-(4-chloro-o-tolyl)formimidoyl]methylamino]thio]-N-ethyl-p-toluenesulfonamide as white crystals, mp. 98°-99°.

Analysis: Calc'd for $C_{18}H_{22}ClN_3O_2S_2$: C, 52.48; H, 5.38; N, 10.20. C, 52.38; H, 5.44; N, 10.28.

EXAMPLE 12

N-[[[N-(4-chloro-o-tolyl)formimidoyl]methylamino]-thio]-N-t-butyl-p-toluenesulfonamide Following the procedure of Example 2, but substituting N,N'-dithiobis[N-t-butyl-p-toluenesulfonamide] for N,N'-dithiobis[N-isopropyl-p-toluenesulfonamide], the product is prepared. The product is recrystallized from isopropanol to obtain 33.6 g. (76.4% yield) of N-[[[N-(4-chloro-o-tolyl)formimidoyl]methylamino]thio]-N-t-butyl-p-toluenesulfonamide as white crystals. mp. 85°–86°.

Analysis: Calc'd for $C_{20}H_{26}ClN_3O_2S_2$: C, 54.59; H, 5.96; N, 9.55 Found: C, 54.47; H, 5.94; N, 9.58.

EXAMPLE 13

N-[[[N-(4-chloro-o-tolyl)formimidoyl]methylamino]-thio]-N-isopropyl-p-chlorophenylsulfonamide Following the procedure of Example 2, but substituting N,N'-dithiobis[N-isopropyl-p-chlorophenylsulfonamide] for N,N'-dithiobis[N-isopropyl-p-toluenesulfonamide] and chlorine for sulfuryl chloride, the product is prepared. The product is recrystallized from SSB to give 11.5 g. (64% yield) of N-[[[N-(4-chloro-o-tolyl)formimidoyl]methylamino]thio]-N-isopropyl-p-chlorophenylsulfonamide as white crystals, mp. 80°–81.5°.

Analysis: Calc'd for $C_{18}H_{21}Cl_2N_3O_2S_2$: C, 48.43; H, 4.74; N, 9.41. Found: C, 48.51; H, 4.68; N, 9.52.

EXAMPLE 14

N-[[[N-2,4-xylylformimidoyl]methylamino]thio]-N-cyclohexylmethanesulfonamide Following the procedure for Example 2, but substituting N,N'-dithiobis[N-cyclohexylmethanesulfonamide] for N,N'-dithiobis[N-isopropyl-p-toluenesulfonamide], chlorine for sulfuryl chloride, and N-methyl-N'-2,4-xylylformamidine for N-methyl-N'-(4-chloro-o-tolyl)formamidine, the product is prepared. The product is recrystallized from SSB containing a small amount of benzene to give 13.2 g. (45% yield) of N-[[[N-2,4-xylylformimidoyl]methylamino]thio]-N-cyclohexylmethanesulfonamide as white crystals, mp. 84°–86°.

Analysis: Calc'd for $C_{17}H_{27}N_3O_2S_2$: C, 55.23; H, 7.37; N, 11.37. Found: C, 54.95; H, 7.25; N, 11.30.

EXAMPLE 15

N-[[[N-2,4-xylylformimidoyl]methylamino]thio]-N-phenylmethanesulfonamide

Following the procedure for Example 2, but substituting N,N'-dithiobis[N-pheylmethanesulfonamide] for N,N'-dithiobis-[N-isopropyl-p-toluenesulfonamide], chlorine for sulfuryl chloride, and N-methyl-N'-2,4-xylylformamidine for N-methyl-N'-(4-chloro-o-tolyl) formamidine, the product is prepared. The product is recrytallized from ethyl acetate to give 2.0 g. (14% yield) of N-[[[N-2,4-xylylformimidoyl]methylamino]thio]-N-phenylmethanesulfonamide as white crystals, mp. 120°–121.5°.

Analysis: Calc'd for $C_{17}H_{21}N_3O_2S_2$: C, 56.17; H, 5.82; N, 11.56. Found: C, 56.06; H, 5.82; N, 11.40.

EXAMPLE 16

N-[[[N-2,4-xylylformimidoyl]methylamino]thio]-N-isopropylbenzylsulfonamide

Following the procedure of Example 2, but substituting N,N'-dithiobis[N-isopropylbenzylsulfonamide] for N,N'-dithiobis[N-isopropyl-p-toluenesulfonamide], chlorine for sulfuryl chloride, and N-methyl-N'-2,4-xylylformamidine for N-methyl-N'-(2-chloro-o-tolyl)-formamidine, the product is prepared. The product is recrystallized from SSB to give 9.0 g. (56% yield) of N-[[[N-2,4-xylylformimidoyl]methylamino]thio]-N-isopropylbenzylsulfonamide as white crystals, mp. 82°–83.5°.

Analysis: Calc'd for $C_{20}H_{27}N_3O_2S_2$: C, 59.23; H, 6.71; N, 10.36. Found: C, 59.34; H, 6.56; N, 10.51.

EXAMPLE 17

N-[[[N-2,4-xylylformimidoyl]methylamino]thio]-N-isopropyl-p-chlorophenylsulfonamide Following the procedure of Example 2, but substituting N,N'-dithiobis[N-isopropyl-p-chlorophenylsulfonamide] for N,N'-dithiobis[N-isopropyl-p-toluenesulfonamide], chlorine for sulfuryl chloride, and N-methyl-N'-2,4-xylylformamidine for N-methyl-N'-(2-chloro-o-tolyl)formamidine, the product is obtained. The product is recrystallized from SSB to give 10.0 g. (59% yield) of N-[[[N-2,4-xylylformimidoyl]methylamino]thio]-N-isopropyl-p-chlorophenylsulfonamide as white crystals, mp. 93.5°–95°.

Analysis: Calc'd for $C_{19}H_{24}ClN_3O_2S_2$: C, 53.57; H, 5.68; N, 9.86. Found: C, 53.43; H, 5.53; N, 10.01.

EXAMPLE 18

N-[[[N-2,4-xylylformimidoyl]methylamino]thio]-N-p-chlorophenyl-p-toluenesulfonamide Following the procedure of Example 2, but substituting N,N'-dithiobis[N-p-chlorophenyl-p-toluenesulfonamide] for N,N'-dithiobis[N-isopropyl-p-toluenesulfonamide], chlorine for sulfuryl chloride, and N-methyl-N'-2,4-xylylformamidine for N-methyl-N'-(4-chloro-o-tolyl)formamidine, the product is obtained. The product is recrystallized from a mixture of SSB and cyclohexane to give 5.5 g. (29% yield) of N-[[[N-2,4-xylylformimidoyl]methylamino]thio]-N-p-chlorophenyl-p-toluenesulfonamide as white crystals, mp. 86°–87°.

Analysis: Calc'd for $C_{23}H_{24}ClN_3O_2S_2$: C, 58.28; H, 5.10; N, 8.86. Found: C, 58.01; H, 5.19; N, 8.78.

EXAMPLE 19

N-[[[N-(4-chloro-o-tolyl)formimidoyl]methylamino]-thio]-N-p-chlorophenyl-p-toluenesulfonamide Following the procedure of Example 2, but substituting N,N'-dithiobis[N-p-chlorophenyl-p-toluenesulfonamide] for N,N'-dithiobis[N-isopropyl-p-toluenesulfonamide] and chlorine for sulfuryl chloride, the product is obtained. The product is recrystallized from a mixture of ether and Skellysolve F ® followed by two recrystallizations from cyclohexane to give 1.0 g. (10% yield) of N-[[[N-(4-chloro-o-tolyl)formimidoyl]methylamino]-thio]-N-p-chlorophenyl-p-toluenesulfonamide as white crystals, mp. 103°–104°.

Analysis: Calc'd for $C_{22}H_{21}Cl_2N_3O_2S_2$: C, 53.44; H, 4.28; N, 8.50. Found: C, 53.48; H, 4.22; N, 8.09.

EXAMPLE 20

N-[[[N-(4-chloro-o-tolyl)formimidoyl]methylamino]-thio]-N-benzyl-p-toluenesulfonamide Following the procedure of Example 2, but substituting N,N'-dithiobis[N-benzyl-p-toluenesulfonamide] for N,N'-dithiobis[N-isopropyl-p-toluenesulfonamide] and chlorine for sulfuryl chloride, 8.8 g. (93% yield) of N-[[[N-(4-chloro-o-tolyl)formimidoyl]methylamino]-thio]-N-benzyl-p-toluenesulfonamide is obtained as an oil.

Analysis: Calc'd for $C_{23}H_{24}ClN_3O_2S_2$: C, 58.28; H, 5.10; N, 8.86. Found: C, 58.05; H, 5.17; N, 8.81.

NMR (CDCl$_3$-tetramethylsilane) 7.85, 7.25, 4.63, 3.1, 2.4, 2.18$\delta$.

EXAMPLE 21

N-[[[N-(4-chloro-o-tolyl)formimidoyl]methylamino]-thio]-N-2,4-dichlorophenyl-p-toluenesulfonamide Following the procedure of Example 2, but substituting N,N'-dithiobis[N-2,4-dichlorophenyl-p-toluenesulfonamide] for N,N'-dithiobis[N-isopropyl-p-toluenesulfonamide] and chlorine for sulfuryl chloride, the product is obtained. The residue is triturated with methanol and recrystallized from a mixture of SSB and isopropanol to give 0.6 g. (5.7% yield) of N-[[[N-(4-chloro-o-tolyl)formimidoyl]methylamino]thio]-N-2,4-dichlorophenyl-p-toluenesulfonamide as white crystals, mp. 97°-98°.

Analysis: Calc'd for $C_{22}H_{20}Cl_3N_3O_2S_2$: C, 49.96; H, 3.81; N, 7.96. Found: C, 50.11; H, 3.73; N, 7.97.

EXAMPLE 22

N-[[[N-(4-chloro-o-tolyl)formimidoyl]methylamino]-thio]-N-phenyl-p-toluenesulfonamide Following the procedure of Example 2, but substituting N,N'-dithiobis[N-phenyl-p-toluenesulfonamide] for N,N'-dithiobis[N-isopropyl-p-toluenesulfonamide] and chloride for sulfuryl chloride, the product is obtained. The product is recrystallized from SSB to give 3.2 g. (40% yield) of N-[[[N-(4-chloro-o-tolyl)formimidoyl]-methylamino]thio]-N-phenyl-p-toluenesulfonamide as white crystals, mp. 95°-96°.

Analysis: Calc'd for $C_{22}H_{22}ClN_3O_2S_2$: C, 57.44; H, 4.82; N, 9.13. Found: C, 57.79; H, 4.79; N, 9.17.

EXAMPLE 23

N-[[[N-2,4-xylylformimidoyl]methylamino]thio]-N-methylmethanesulfonamide

Following the procedure of Example 3, but substituting N-methylmethanesulfonamide for N-isopropyl-p-toluenesulfonamide, the product is obtained. The product is recrystallized from SSB followed by recrystallization from isopropanol to give 8.0 g. (27% yield) of N-[[[N-2,4-xylylformimidoyl]methylamino]thio]-N-methylmethanesulfonamide as white crystals, mp. 63°-64°.

Analysis: Calc'd for $C_{12}H_{19}N_3O_2S_2$: C, 47.82; H, 6.35; N, 13.94. Found: C, 47.85; H, 6.53; N, 14.20.

EXAMPLE 24

N-[[[N-2,4-dichlorophenylformimidoyl]methylamino]-thio]-N-isopropyl-p-toluenesulfonamide Following the procedure of Example 3, but substituting N-methyl-N'-2,4-dichlorophenylformamidine for N-methyl-N'-2,4-xylylformamidine, the product is obtained. The product is recrystallized from methanol to give 11.0 g. (49% yield) of N-[[[-N-2,4-dichlorophenyl-formimidoyl]methylamino]thio]N-isopropyl-p-toluenesulfonamide as white crystals, mp. 79°-81°.

Analysis: Calc'd for $C_{18}H_{21}Cl_2N_3O_2S_2$: C, 48.43; H, 4.74; N, 9.41. Found: C, 48.63; H, 4.80; N, 9.55.

EXAMPLE 25

N-[[[N-(2-chloro-p-tolyl)-formimidoyl]methylamino]-thio]-N-isopropyl-p-toluenesulfonamide Following the procedure of Example 3, but substituting N-methyl-N'-(2-chloro-p-tolyl)formamidine for N-methyl-N'-2,4-xylylformamidine, the product is obtained. The product is recrystallized from methanol to give 8.0 g. (47% yield) of N-[[[N-(2-chloro-p-tolyl)for-mimidoyl]methylamino]thio]-N-isopropyl-p-toluenesulfonamide as white crystals, mp. 101°-103°.

Analysis: Calc'd for $C_{19}H_{24}ClN_3O_2S_2$: C, 53.57; H, 5.68; N, 9.86. Found: C, 53.60; H, 5.71; N, 9.94.

EXAMPLE 26

Following the procedure of Example 3, but substituting N-methyl-N'-(4-chloro-o-tolyl)formamidine for N-methyl-N'-2,4-xylylformamidine and the appropriate N-substituted sulfonamide (V)

(V)

wherein $R_3$ and $R_4$ are as defined in Table 1 for N-isopropyl-p-toluenesulfonamide, the corresponding product of this invention (VI) is obtained

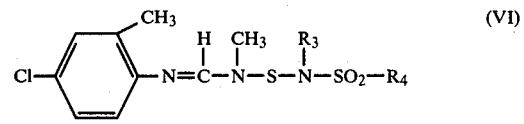

(VI)

wherein $R_3$ and $R_4$ are defined in Table 1.

TABLE 1

| $R_3$ | $R_4$ |
| --- | --- |
| 1. methyl | phenyl |
| 2. ethyl | methyl |
| 3. ethyl | phenyl |
| 4. n-propyl | methyl |
| 5. n-propyl | phenyl |
| 6. n-propyl | p-tolyl |
| 7. n-butyl | methyl |
| 8. n-butyl | phenyl |
| 9. n-butyl | p-tolyl |
| 10. t-butyl | phenyl |
| 11. benzyl | phenyl |
| 12. cyclohexyl | phenyl |
| 13. cyclohexyl | p-tolyl |
| 14. phenyl | phenyl |
| 15. p-chlorophenyl | methyl |
| 16. phenethyl | p-tolyl |
| 17. p-nitrophenyl | methyl |
| 18. p-trifluoromethylphenyl | methyl |
| 19. p-methoxyphenyl | methyl |
| 20. p-cyanophenyl | methyl |

EXAMPLE 27

Following the procedure of Example 3, but substituting the appropriate N-substituted sulfonamide (V) wherein $R_3$ and $R_4$ are as defined in Table 2 for N-isopropyl-p-toluenesulfonamide the corresponding product of this invention (VII) is obtained

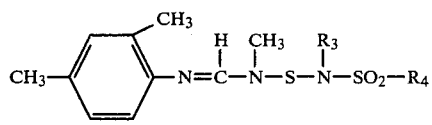

(VII)

wherein $R_3$ and $R_4$ are as defined in Table 2.

TABLE 2

| | $R_3$ | $R_4$ |
|---|---|---|
| 1. | methyl | p-tolyl |
| 2. | methyl | benzyl |
| 3. | ethyl | methyl |
| 4. | ethyl | phenyl |
| 5. | ethyl | p-tolyl |
| 6. | n-propyl | methyl |
| 7. | n-propyl | phenyl |
| 8. | n-propyl | p-tolyl |
| 9. | isopropyl | methyl |
| 10. | isopropyl | phenyl |
| 11. | benzyl | methyl |
| 12. | benzyl | p-tolyl |
| 13. | cyclohexyl | phenyl |
| 14. | cyclohexyl | p-tolyl |
| 15. | phenyl | p-tolyl |
| 16. | phenethyl | p-tolyl |
| 17. | isopropyl | phenethyl |
| 18. | methyl | benzyl |
| 19. | methyl | p-chlorophenyl |
| 20. | methyl | p-nitrophenyl |
| 21. | methyl | p-trifluoromethylphenyl |
| 22. | methyl | p-methoxyphenyl |
| 23. | methyl | p-cyanophenyl |

EXAMPLE 28

Following the procedure of Example 3, but substituting N-methyl-N'-(4-bromo-o-tolyl)formamidine for N-methyl-N'-2,4-xylylformamidine and the appropriate N-substituted sulfonamide (V) wherein $R_3$ and $R_4$ are as defined in Table 3 for N-isopropyl-p-toluenesulfonamide, the corresponding product of this invention (VIII) is obtained

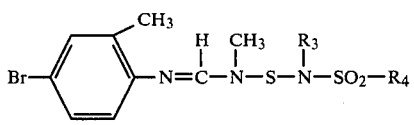

(VIII)

wherein $R_3$ and $R_4$ are as defined in Table 3.

TABLE 3

| | $R_3$ | $R_4$ |
|---|---|---|
| 1. | methyl | methyl |
| 2. | methyl | p-tolyl |
| 3. | phenyl | methyl |
| 4. | cyclohexyl | methyl |
| 5. | isopropyl | benzyl |
| 6. | isopropyl | p-tolyl |
| 7. | phenyl | p-tolyl |
| 8. | methyl | phenyl |

EXAMPLE 29

Following the procedure of Example 3, but substituting N-methyl-N'-(4-chloro-2-ethylphenyl)formamidine for N-methyl-N'-2,4-xylylformamidine and the appropriate N-substituted sulfonamide (V) wherein $R_3$ and $R_4$ are as defined in Table 4 for N-isopropyl-p-toluenesulfonamide, the corresponding product of this invention (IX) is obtained

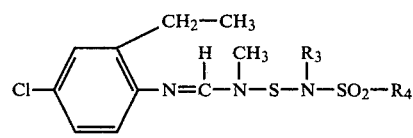

(IX)

wherein $R_3$ and $R_4$ are as defined in Table 4.

TABLE 4

| | $R_3$ | $R_4$ |
|---|---|---|
| 1. | methyl | methyl |
| 2. | methyl | p-tolyl |
| 3. | cyclohexyl | methyl |
| 4. | phenyl | p-tolyl |

EXAMPLE 30

Following the procedure of Example 3, but substituting N-methyl-N'-(2,4-dichlorophenyl)formamidine for N-methyl-N'-2,4-xylylformamidine and the appropriate N-substituted sulfonamide (V) wherein $R_3$ and $R_4$ are as defined in Table 5 for N-isopropyl-p-toluenesulfonamide, the corresponding product of this invention (X) is obtained.

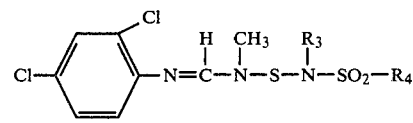

(X)

wherein $R_3$ and $R_4$ are as defined in Table 5.

TABLE 5

| | $R_3$ | $R_4$ |
|---|---|---|
| 1. | methyl | methyl |
| 2. | methyl | phenyl |
| 3. | methyl | p-tolyl |
| 4. | ethyl | phenyl |
| 5. | ethyl | p-tolyl |
| 6. | isopropyl | methyl |
| 7. | isopropyl | phenyl |
| 8. | isopropyl | p-tolyl |
| 9. | benzyl | methyl |
| 10. | benzyl | phenyl |
| 11. | benzyl | p-tolyl |
| 12. | cyclohexyl | methyl |
| 13. | cyclohexyl | phenyl |
| 14. | cyclohexyl | p-tolyl |
| 15. | phenyl | methyl |
| 16. | phenyl | phenyl |
| 17. | phenyl | p-tolyl |
| 18. | isopropyl | benzyl |
| 19. | isopropyl | phenethyl |
| 20. | p-chlorophenyl | methyl |
| 21. | phenethyl | p-tolyl |
| 22. | p-nitrophenyl | methyl |
| 23. | p-trifluoromethylphenyl | methyl |
| 24. | p-methoxyphenyl | methyl |
| 25. | p-cyanophenyl | methyl |
| 26. | methyl | benzyl |
| 27. | methyl | p-chlorophenyl |
| 28. | methyl | p-nitrophenyl |
| 29. | methyl | p-trifluoromethylphenyl |
| 30. | methyl | p-methoxyphenyl |
| 31. | methyl | p-cyanophenyl |

EXAMPLE 31

Following the procedure of Example 3, but substituting N-methyl-N'-(2-chloro-p-tolyl)formamidine for N-methyl-N'-2,4-xylylformamidine and the appropriate N-substituted sulfonamide (V) wherein $R_3$ and $R_4$ are as defined in Table 6 for N-isopropyl-p-toluenesulfonamide, the corresponding product of this invention (XI) is obtained.

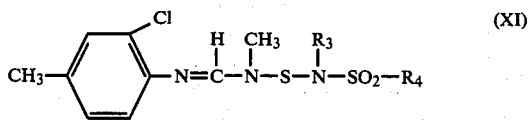

wherein $R_3$ and $R_4$ are defined in Table 6.

TABLE 6

| $R_3$ | $R_4$ |
|---|---|
| 1. methyl | methyl |
| 2. methyl | phenyl |
| 3. methyl | p-tolyl |
| 4. ethyl | phenyl |
| 5. ethyl | p-tolyl |
| 6. isopropyl | methyl |
| 7. isopropyl | phenyl |
| 8. isopropyl | p-tolyl |
| 9. benzyl | methyl |
| 10. benzyl | phenyl |
| 11. benzyl | p-tolyl |
| 12. cylcohexyl | methyl |
| 13. cyclohexyl | phenyl |
| 14. cyclohexyl | p-tolyl |
| 15. phenyl | methyl |
| 16. phenyl | phenyl |
| 17. phenyl | p-tolyl |
| 18. isopropyl | benzyl |
| 19. isopropyl | phenethyl |
| 20. p-chlorophenyl | methyl |
| 21. phenethyl | p-tolyl |
| 22. p-nitrophenyl | methyl |
| 23. p-trifluoromethylphenyl | methyl |
| 24. p-methoxyphenyl | methyl |
| 25. p-cyanophenyl | methyl |
| 26. methyl | benzyl |
| 27. methyl | p-chlorophenyl |
| 28. methyl | p-nitrophenyl |
| 29. methyl | p-trifluoromethylphenyl |
| 30. methyl | p-methoxyphenyl |
| 31. methyl | p-cyanophenyl |

EXAMPLE 32

Following the procedure of Example 3, but substituting N-methyl-N'-(2-bromo-p-tolyl)formamidine for N-methyl-N'-2,4-xylylformamidine and the appropriate N-substituted sulfonamide (V) wherein $R_3$ and $R_4$ are as defined in Table 7 for N-isopropyl-p-toluenesulfonamide, the corresponding product of this invention (XII) is obtained.

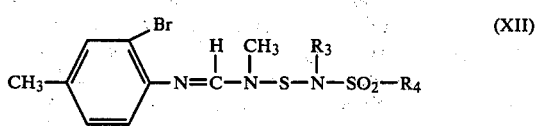

wherein $R_3$ and $R_4$ are as defined in Table 7.

TABLE 7

| $R_3$ | $R_4$ |
|---|---|
| 1. methyl | methyl |
| 2. methyl | p-tolyl |
| 3. phenyl | methyl |
| 4. cyclohexyl | methyl |
| 5. isopropyl | benzyl |
| 6. isopropyl | p-tolyl |
| 7. phenyl | p-tolyl |
| 8. methyl | phenyl |

EXAMPLE 33

Following the procedure of Example 3, but substituting N-methyl-N'-(2-chloro-4-ethylphenyl)formamidine for N-methyl-N'-2,4-xylylformamidine and the appropriate N-substituted sulfonamide (V) wherein $R_3$ and $R_4$ are as defined in Table 8 for N-isopropyl-p-toluenesulfonamide, the corresponding product of this invention (XIII) is obtained.

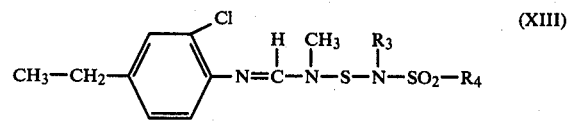

wherein $R_3$ and $R_4$ are as defined in Table 8.

TABLE 8

| $R_3$ | $R_4$ |
|---|---|
| 1. methyl | methyl |
| 2. methyl | p-tolyl |
| 3. cyclohexyl | methyl |
| 4. phenyl | p-tolyl |

The compounds of Formula I are particularly advantageous commercially as arthropodal pesticides. For example they are relatively stable both in storage and upon application in the field thus providing long-lasting residual effectiveness.

In addition to killing arthropod pests on contact, the compounds of the invention are absorbed by the vascular system of many plants, for example by cotton plants, and act systemically to kill the pests feeding upon the plant. Thus, their period of pesticidal activity is further extended and non-feeding arthropods, e.g., insects not harmful to the plant, are not unnecessarily killed during the whole period of pesticidal activity.

Compounds of the invention are also ovicidal, and are particularly effective in the control of acarine pest populations by this ovicidal action. Lepidopterous ova are also particularly susceptible to the compounds of the invention.

The compounds of the Formula I are also advantageous in that they exhibit relatively low mammalian toxicity and are non-phytotoxic at effective concentrations.

The invention also comprises compositions for arthropod control which comprise an acceptable carrier and an effective amount of a compound of the invention. The compositions are useful in the method of the invention which is a process for controlling invertebrate pests, which comprises applying to a situs, effective amounts of the compounds of the invention.

By the term "situs" is meant plants such as ornamentals, food crops, fruit trees, textile producing plants, berry bushes, and lumber forests; animals, particularly domestic animals; farm yards; animal shelters; buildings; sanitary land-fill areas; ponds and standing water; and like sites which are infected with or are potential infestation sites for invertebrate pests controllable with the compounds of the invention.

The novel compounds of the invention are useful in controlling invertebrate pest populations, e.g., in killing adults, larvae, and ova of invertebrate pests or animals of the Phylum Arthropoda, for example those of Class Insecta such as those of the order Coleoptera as illustrated by the cotton boll weevil (*Anthonomus grandis* Boheman); those of the order Lepidoptera as illustrated by the southern army worm (*Spodoptera eridania* Cramer); those of Class Arachnida such as those of the order Acarina as illustrated by the two-spotted spider mite (*Tetranychus telarius* Linnaeus or *Tetranychus urticae* Koch).

In addition to controlling pest populations through their lethal effect, the compounds are also useful in control through their effect as behavioral modifiers. For example, young lepidopteran larvae, aphids, ticks, and mites are repelled by the chemicals or by treated foliage or animals, resulting in a marked reduction in population density. Adult moths are affected and ovipost less on treated plant parts. In addition to being repelled, mites exhibit spindown and walkdown activity from treated foliage.

The compounds of this invention may be employed in their pure forms to control invertebrate pest populations. However, it is preferred that they be applied to a situs in the form of a composition, comprising the compound and an acceptable diluent or carrier. The concentration of the active compound can range from about 0.001% to about 96% w/w depending on the type of composition, the solubility of the compound, the pest to be controlled, etc. Acceptable carriers or diluents are well known in the art. For example, those compounds which are solids at ambient temperatures may be formulated as granulars, dusts, wettable powders, emulsifiable concentrates, aqueous dispersions, solutions, and flowable creams for application to insects, mites, ticks, objects, or other situs. Those compounds which are liquids at ambient temperatures may be formulated as emulsifiable concentrates, aqueous dispersions, suspensions, solutions, aerosols, dusts, granulars, and the like.

The compounds (I) of the invention may also be admixed with other known pesticides to form compositions of the invention. For example, they may be mixed with malathion, azinphosmethyl, carbaryl, methoxychlor, and like pesticidal compounds.

Illustratively, dusts are readily formulated by grinding a mixture of the solid compounds (I) and a pulverulent carrier in the presence of each other. Grinding is conveniently accomplished in a ball mill, a hammer mill, or by air-blast micronization. A preferred ultimate particle size is less than 60 microns. Preferably, 95% of the particles are less than 50 microns, and about 75% are 5 to 20 microns. Dusts of that degree of comminution are conveniently free flowing and can be applied to inanimate matter, fruit trees, crop plants, animals, and soil so as to effect thorough distribution and coverage. Dusts are particularly adapted for effectively controlling invertebrate pests such as insects and mites over wide areas when applied by airplane. They are also indicated for application to the undersides of plant foliage.

Representative pulverulent diluent carriers which are acceptable are the natural clays such as attapulgite, kaolin (e.g., China and Barden), and montmorillonite (e.g., bentonite); minerals in their natural forms as they are obtained from the earth such as talc, pyrophyllite, quartz, diatomaceous earth, fuller's earth, chalk, rock phosphates and sulfates, sulfur, silica and silicates; chemically modified minerals such as washed bentonite, precipitated calcium silicate, synthetic magnesium silicate, and colloidal silica; and organic flours such as wood, walnut shell, soybean, cottonseed, and tobacco flours, and free-flowing hydrophobic starches.

Dusts may also be prepared by dissolving a compound (I) in a volatile solvent such as methylene chloride, mixing the solution with a pulverulent diluent carrier and evaporating the solvent.

The proportions of pulverulent carrier and compound (I) may be varied over a wide range depending upon the pests to be controlled and the conditions of treatment. In general, dust formulations contain up to about 50% (on a weight basis) of the compound (I) as the active ingredient. Dusts having as little as 0.001% of the active ingredient may be used, but a generally preferred proportion is from about 1% to about 10% of the compound.

Wettable powder formulations are prepared by incorporating a surfactant in a dust composition prepared as described above. By incorporating from 0.1% to about 12% of a surfactant in a dust, a wettable powder is obtained which is particularly adapted for further admixture with water for spraying on inanimate matter and products, fruit trees, field crops, animals, and soil. Such wettable powders may be admixed with water to obtain any desired concentration of compound (I) and the mixture may be applied in amounts sufficient to obtain predetermined rates of application and uniform distribution. Preferably wettable powders contain from about 10 percent to about 80 percent by weight of compound (I) as the active ingredient.

The surfactants employed may be characterized as capable of reducing the surface tension of water to less than about 40 dynes per centimeter in concentrations of about 1% or less.

Representative surfactants conventionally employed for preparing wettable powder formulations include alkyl sulfates and sulfonates, alkyl aryl sulfonates, sulfosuccinate esters, polyoxyethylene sulfate, polyoxyethylenesorbitan monolaurate, alkyl-aryl polyether sulfates, alkylaryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, and the like. The preferred class of surfactants for preparing compositions of this invention are blends of sulfonated oils and polyalcohol carboxylic acid esters such as the commercially available Emcol H-77 ®, blends of polyoxyethylene ethers and oil-soluble sulfonates such as commercially available Emcol H-400 ®, blends of alkyl aryl sulfonates and alkylphenoxy polyethoxy ethanols such as the commercially available Tritons X-151, X-161, and X-171 ®, e.g. about equal parts of sodium dodecylbenzenesulfonate and isooctylphenoxy polyethoxy ethanol containing about 12 ethoxy groups, and blends of calcium alkyl-aryl sulfonates and polyethoxylated vegetable oils such as commercially available Agrimul N4S ®. The sulfate and sulfonate surfactants discussed above are preferably used in the form of their soluble salts, for example, their sodium salts.

If desired, dispersants such as methyl cellulose, polyvinyl alcohol, sodium ligninsulfonates, and the like may be included in the wettable powder compositions of this invention. Adhesive or sticking agents such as vegetable oils, naturally occurring gums, casein, and others may also be included. If unlined storage or shipping drums are to be used a corrosion inhibitor may be added. Likewise, anti-foaming agents such as stearic acid may be added.

Granular compositions of this invention are convenient for application to soil when persistence is desired. Such compositions are readily applied by broadcast or by localized, e.g., in-the-row applications. The individual granules may be any desired size from 30 to 60 mesh up to 20 to 40 mesh, or even larger. Granulars are prepared by dissolving the active compound in a solvent such as methylene chloride, xylene, or acetone and applying the solution to a quantity of a granulated absorbent carrier. Representative granulated absorbent carriers are ground corn cobs, ground walnut shells, ground peanut hulls, and the like. When desired, the impregnated granulated absorbent carrier may be coated with a coating that will preserve the integrity of the granular until it is applied to an object or situs favorable for release of the active ingredient. Such coatings are well known in the art.

The compounds (I) of the invention may be applied to the pests themselves or to a situs in aqueous sprays without a solid carrier. Such aqueous sprays are advantageous for certain types of spray equipment and conditions of application as is well known in the art. They are also advantageous when uniform dispersions, homogeneous solutions, or other easily mixed aqueous sprays are desired.

Aqueous sprays without a solid carrier are prepared from concentrated solutions of the compounds (I) of the invention in an inert organic solvent carrier. The inert organic solvent carrier may be one that is miscible or immiscible with water. The compounds (I) that are somewhat soluble in water may be dissolved in a water miscible solvent carrier, e.g., ethanol, and mixed with water to give homogeneous solutions. The compounds (I) that are less soluble in water may be dissolved in a solvent carrier that is immiscible with water and the solution dispersed in water to give a uniform dispersion, e.g., an emulsion.

In an oil-in-water emulsion, the solvent phase is dispersed in the water phase and the dispersed phase contains the compound (I). In this way, uniform distribution of a water insoluble compound (I) is achieved in an aqueous spray. A solvent carrier in which the compounds (I) are highly soluble is desirable so that relatively high concentrations of the compound (I) can be obtained. One or more solvent carriers with or without a co-solvent may be used in order to obtain concentrated solutions of the compounds (I), the main consideration being to employ a water-immiscible solvent for the compound (I) that will hold the compound in solution over the range of concentrations useful for applying to invertebrate pests or a situs.

The emulsifiable concentrate compositions of the invention are preferred compositions prepared by dissolving the compound (I) as the active ingredient and a surfactant such as one of those previously described, in a substantially water-immiscible solvent carrier (i.e., a solvent carrier which is soluble in water to the extent of less than 2.5% by volume at temperatures of the order of 20° C. to 30° C.), for example: summer oils (a paraffinic, intermediate distillation fraction having a viscosity range from 40 to 85 seconds Saybolt and an unsulfonatable residue over 90 percent); ethylene dichloride; aromatic hydrocarbons such as benzene, toluene, and xylene; and high-boiling petroleum hydrocarbons such as kerosene, diesel oil, high flash (>38° C.) xylene-range solvent (e.g., Tenneco 500-100 ®), and the like. When desired, a co-solvent such as methyl ethyl ketone, acetone, isopropanol, and the like may be included with the solvent carrier in order to enhance the solubility of the compound (I). Aqueous emulsions are prepared by mixing the concentrate with water to give the desired concentration of compound.

Advantageously, the concentration of compound (I) in emulsifiable concentrates will range from about 5 percent to about 50 percent by weight, preferably from about 10 percent to about 40 percent. A concentrate comprising 20 percent by weight of the compound (I) dissolved in a water-immiscible solvent of the kind noted above may be admixed with an aqueous medium in the proportions of 13 ml. of concentrate with 1 gal. of medium to give a mixture containing 700 parts of compounds (I) per million parts of liquid carrier. Similarly, 1 qt. of a 20 percent concentrate mixed with 40 gals. of water provides about 1200 ppm (parts per million) of a compound (I). In the same manner, more concentrated solutions of active ingredient may be prepared by adjusting upward the proportion of compound (I).

The above described concentrate compositions of the invention which are intended for use in the form of aqueous dispersions or emulsions may also advantageously contain a humectant, i.e., an agent which will delay the drying of the composition in contact with material to which it has been applied. Conventionally used humectants are exemplified by glycerol, diethylene glycol, solubilized lignins such as calcium ligninsulfonate, and the like.

For use in an aerosol, the compound (I) may be dissolved in acetone or a mixture of acetone and a heavy petroleum oil and mixed in a thick-walled canister or bomb with a propellant such as methyl chloride or dichlorodifluoromethane.

The compositions containing compounds (I) of the invention may be applied to invertebrate pests or pestiferous sites by conventional methods. For example, an area of soil, buildings, animals, or plants may be treated by spraying emulsions, or solutions from hand-operated knapsack sprayers. Creams and ointment formulations may be applied to a situs for prolonged protection from insects, mites, and ticks. As an alternative to spraying, an appropriate situs may be treated by dipping; e.g., domestic animals can be walked through a bath of a composition of the invention.

It will of course be appreciated by those skilled in the art that the conditions encountered when applying the method and compositions of this invention to actual practice can vary widely. Among the variables that may be encountered are the degree of infestation by pests, the particular pest to be controlled, the specific compound (I) employed, the particular situs being treated, the age or degree of development of plants to be protected, the prevailing weather conditions, such as temperature, relative humidity, rainfall, dew and like environmental conditions. Dependent upon the variables encountered in a given situation, the amount of compounds (I) to be employed as an effective amount, the frequency of application and the technique of application will be adjusted for optimum effect, as those skilled in the art well appreciate.

In general, efficacy of the compounds (I) against invertebrate pests has been demonstrated at concentrations of 1000, 500, 100, 50 and even 30 ppm by weight of the novel compounds (I) depending upon the specific pest to be controlled. Some invertebrate animal pests will be more sensitive to the compounds (I) than others. Methods of testing a given compound (I) to determine the minimum effective concentration required for killing a specific invertebrate pest are well known; see for example U.S. Pat. Nos. 3,474,170; 3,476,836; and 3,478,029. In general, effective amounts of the compounds (I) for pesticidal activity is obtained when the compounds (I) are applied at concentrations of about 30 to about 6000 ppm, preferably at concentrations of about 100 to about 4000 ppm.

The following examples illustrate compositions of the invention.

EXAMPLE 34

A wettable powder formulation is obtained by blending and milling 327 lbs. of Georgia Clay, 4.5 lbs. of isooctylphenoxy ethanol (Triton X-100 ®) as a wetting agent, 9 lbs. of a polymerized sodium salt of substituted benzoic long-chain sulfonic acid (Daxad 27 ®) as a dispersing agent, and 113 lbs. of N-[[[N-(4-chloro-o-tolyl)-formimidoyl]methylamino]thio]-N-isopropyl-p-toluenesulfonamide (Example 2). The resulting formulation has the following percentage composition (parts herein are by weight unless otherwise specified).

| | |
|---|---|
| N—[[[N—(4-chloro-o-tolyl)-formimidoyl]methylamino]thio]-N—isopropyl-p-toluenesulfonamide | 25% |
| Isooctylphenoxy polyethoxy ethanol | 1% |
| Polymerized sodium salt of substituted benzoid long-chain sulfonic acid | 2% |
| Georgia Clay | 72% |

This formulation, when dispersed in water at the rate of 10 lbs. per 100 gals., gives a spray formulation containing about 0.3% (3000 ppm) active ingredient which can be applied to invertebrate pests, plants, or other invertebrate pest habitats or invertebrate pest foods to kill such pests or control them through behavior modification.

Similarly, replacing the arylformamidine sulfonamide as used in the above example with an equal proportion of any other compound of the formula (I) as prepared in Examples 3 through 19 and 21 through 33, a pesticidal composition is obtained which will control invertebrate pests.

EXAMPLE 35

An emulsifiable concentrate having the following percentage composition:

| | |
|---|---|
| N—[[[N—(4-chloro-o-tolyl)-formimidoyl]methylamino]thio]-N—methyl-p-toluenesulfonamide (Example 1) | 15.0% |
| High-flash (>38° C.) xylene-range solvent (e.g., Tenneco 500-100 ®) | 80.0% |
| Blend of alkyl aryl sulfonates and alkylphenoxy polyethoxy ethanols (Triton X-151 ®) | 5.0% | is obtained by mixing 15.0 pounds of N-[[[N-(4-chloro-o-tolyl)-formimidoyl]methylamino]thio]-N-methyl-p-toluenesulfonamide (Example 1), 80 pounds of Tenneco 500–100, and 5.0 pounds of Triton X-151.

6.67 Lbs. of the concentrate mixed with 10 gals. of water gives a spray emulsion containing about 11,000 ppm. of active ingredient which can be applied to invertebrate pests, plants, or other invertebrate pest habitats or invertebrate pest foods to kill such pests or control them through behavior modification.

Similarly, replacing the arylformamidine sulfonamide used in the above example with an equal proportion of the compound prepared in Examples 2 through 33, a pesticidal composition is obtained which will control invertebrate pests.

What is claimed is:

1. A compound of the formula

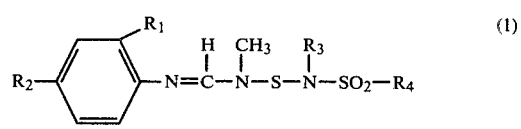

wherein $R_1$ is chloro, bromo, or alkyl of one through four carbon atoms;

$R_2$ is hydrogen, chloro, bromo, or alkyl of one through four carbon atoms;

$R_3$ is phenalkyl wherein alkyl is one or two methylene units in length, or phenyl where the phenyl is unsubstituted or substituted with one through three substituents selected from the group consisting of methyl, chloro, bromo, nitro, trifluoromethyl, alkoxy of one or two carbon atoms, and cyano; and $R_4$ is phenalkyl wherein alkyl is one or two methylene units in length and where the phenyl is unsubstituted or substituted with one through three substituents selected from the group consisting of methyl, chloro, bromo, nitro, trifluoromethyl, alkoxy of one or two carbon atoms, and cyano, or phenyl where the phenyl is unsubstituted or substituted with a substituent selected from the group consisting of methyl, chloro and bromo.

2. A compound according to claim 1 wherein $R_1$ is methyl;

$R_2$ is selected from the group consisting of methyl, chloro, and bromo;

$R_3$ is phenalkyl wherein alkyl is one or two methylene units in length, or phenyl where the phenyl is unsubstituted or substituted with one through three substituents selected from the group consisting of methyl, chloro, and bromo; and $R_4$ is phenalkyl wherein alkyl is one or two methylene units in length and where the phenyl is unsubstituted or substituted with one through three substituents selected from the group consisting of methyl, chloro, bromo, nitro, trifluoromethyl, alkoxy of one or two carbon atoms, and cyano, or phenyl where the phenyl is unsubstituted or substituted with a substituent selected from the group consisting of methyl, chloro, and bromo.

3. A compound according to claim 2 which is N-[[[N-(4-chloro-o-tolyl)-formimidoyl]methylamino]thio]-N-benzylmethanesulfonamide.

4. A compound according to claim 2 which is N-[[[N-(4-chloro-o-tolyl)-formamidoyl]methylamino]thio]-N-phenylmethanesulfonamide.

5. A compound according to claim 2 which is N-[[[N-(4-chloro-o-tolyl)-formimidoyl]methylamino]thio]-N-isopropylbenzylsulfonamide.

6. A compound according to claim 2 which is N-[[[N-2,4-xylylformimidoyl]methylamino]thio]-N-phenylmethanesulfonamide.

7. A compound according to claim 2 which is N-[[[N-2,4-xylylformimidoyl]methylamino]thio]-N-isopropylbenzylsulfonamide.

8. A compound according to claim 2 which is N-[[[N-2,4-xylylformimidoyl]methylamino]thio]-N-p-chlorophenyl-p-toluenesulfonamide.

9. A compound according to claim 2 which is N-[[[N-(4-chloro-o-tolyl)formimidoyl]methylamino]thio]-N-p-chlorophenyl-p-toluenesulfonamide.

10. A compound according to claim 2 which is N-[[[N-(4-chloro-o-tolyl)formimidoyl]methylamino]thio]-N-benzyl-p-toluenesulfonamide.

11. A compound according to claim 2 which is N-[[[N-(4-chloro-o-tolyl)formimidoyl]methylamino]thio]-N-2,4-dichlorophenyl-p-toluenesulfonamide.

12. A compound according to claim 2 which is N-[[[N-(4-chloro-o-tolyl)formimidoyl]methylamino]thio]-N-phenyl-p-toluenesulfonamide.

13. A process for controlling arthropodal pest populations which comprises applying to a situs an effective amount of a compound of the formula:

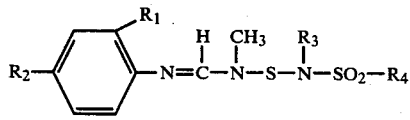

wherein
- R₁ is chloro, bromo, or alkyl of one through four carbon atoms;
- R₂ is hydrogen, chloro, bromo, or alkyl of one through four carbon atoms;
- R₃ is phenalkyl wherein alkyl is one or two methylene units in length, or phenyl where the phenyl is unsubstituted or substituted with one through three substituents selected from the group consisting of methyl, chloro, bromo, nitro, trifluoromethyl, alkoxy of one or two carbon atoms, and cyano; and
- R₄ is phenalkyl wherein alkyl is one or two methylene units in length and where the phenyl is unsubstituted or substituted with one through three substituents selected from the group consisting of methyl, chloro, bromo, nitro, trifluoromethyl, alkoxy of one or two carbon atoms, and cyano, or phenyl where the phenyl is unsubstituted or substituted with a substituent selected from the group consisting of methyl, chloro and bromo.

14. The process of claim 13 wherein R₁ in the compound applied is alkyl of one through four carbon atoms.

15. The process of claim 14 wherein the compound applied is N-[[[N-(4-chloro-o-tolyl)-formimidoyl]methylamino]thio]-N-benzylmethanesulfonamide.

16. The process of claim 14 wherein the compound applied is N-[[[N-(4-chloro-o-tolyl)formimidoyl]methylamino]thio]-N-phenylmethanesulfonamide.

17. The process of claim 14 wherein the compound applied is N-[[[N-(4-chloro-o-tolyl)formimidoyl]methylamino]thio]-N-isopropylbenzylsulfonamide.

18. The process of claim 14 wherein the compound applied is N-[[[N-2,4-xylylformimidoyl]methylamino]thio]-N-phenylmethanesulfonamide.

19. The process of claim 14 wherein the compound applied is N-[[[N-2,4-xylylformimidoyl]methylamino]thio]-N-isopropylbenzylsulfonamide.

20. The process of claim 14 wherein the compound applied is N-[[[N-2,4-xylylformimidoyl]methylamino]thio]-N-p-chlorophenyl-p-toluenesulfonamide.

21. The process of claim 14 wherein the compound applied is N-[[[N-(4-chloro-o-tolyl)formimidoyl]methylamino]thio]-N-p-chlorophenyl-p-toluenesulfonamide.

22. The process of claim 14 wherein the compound applied is N-[[[N-(4-chloro-o-tolyl)formimidoyl]methylamino]thio]-N-benzyl-p-toluenesulfonamide.

23. The process of claim 14 wherein the compound applied is N-[[[N-(4-chloro-o-tolyl)formimidoyl]methylamino]thio]-N-2,4-dichlorophenyl-p-toluenesulfonamide.

24. The process of claim 14 wherein the compound applied is N-[[[N-(4-chloro-o-tolyl)formimidoyl]methylamino]thio]-N-phenyl-p-toluenesulfonamide.

25. The process of claim 13 for controlling insect pest populations.

26. The process of claim 13 for controlling arachnid pest populations.

27. The process of claim 13 for killing insect pest populations.

28. The process of claim 13 for killing arachnid pest populations.

29. The process of claim 13 for controlling ticks.

30. A composition for controlling arthropodal pest populations comprising an acceptable carrier in association with an effective amount of a compound of the formula:

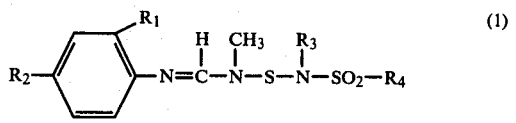

wherein
- R₁ is chloro, bromo, or alkyl of one through four carbon atoms;
- R₂ is hydrogen, chloro, bromo, or alkyl of one through four carbon atoms;
- R₃ is phenalkyl wherein alkyl is one or two methylene units in length, or phenyl where the phenyl is unsubstituted or substituted with one through three substituents selected from the group consisting of methyl, chloro, bromo, nitro, trifluoromethyl, alkoxy of one or two carbon atoms, and cyano; and
- R₄ is phenalkyl wherein alkyl is one or two methylene units in length and where the phenyl is unsubstituted or substituted with one through three substituents selected from the group consisting of methyl, chloro, bromo, nitro, trifluoromethyl, alkoxy of one or two carbon atoms, and cyano, or phenyl where the phenyl is unsubstituted or substituted with a substituent selected from the group consisting of methyl, chloro and bromo.

31. The composition of claim 30 wherein the concentration of the compound (I) is from about 0.001% to about 96% by weight of said composition.

32. The composition of claim 30 wherein
- R₁ is chloro, bromo, or methyl;
- R₂ is selected from the group consisting of methyl, chloro, and bromo;

$R_3$ is phenalkyl wherein alkyl is one or two methylene units in length, or phenyl where the phenyl is unsubstituted or substituted with one through three substituents selected from the group consisting of methyl, chloro, and bromo; and $R_4$ is phenalkyl wherein alkyl is one or two methylene units in length and where the phenyl is unsubstituted or substituted with one through three substituents selected from the group consisting of methyl, chloro, bromo, nitro, trifluoromethyl, alkoxy of one or two carbon atoms, and cyano, or phenyl where the phenyl is unsubstituted or substituted with a substituent selected from the group consisting of methyl, chloro, and bromo.

33. The agricultural composition of claim 32 wherein the concentration of the compound (I) is from about 0.001% to about 96% by weight of said composition.

34. The composition of claim 32 wherein $R_1$ is chloro or bromo.

35. The composition of claim 32 wherein $R_1$ is methyl.

36. The composition of claim 30 for controlling insects.

37. The composition of claim 30 for controlling arachnids.

38. The composition of claim 30 for controlling ticks.

39. The composition of claim 30 where the compound is N-[[[N-2,4-xylylformimidoyl]methylamino]thio]-N-isopropylbenzylsulfonamide.

* * * * *